(12) United States Patent
Bowman et al.

(10) Patent No.: US 12,103,906 B2
(45) Date of Patent: *Oct. 1, 2024

(54) CLUSTER COMPOUNDS AND METHODS OF MAKING THE SAME

(71) Applicant: Earth Science Laboratories, Inc., Rogers, AR (US)

(72) Inventors: Reid Henry Bowman, Fort Collins, CO (US); David Nicholas, Gulf Breeze, FL (US); Freddie L. Singleton, Fruit Cove, FL (US)

(73) Assignee: Earth Science Laboratories, Inc., Rogers, AR (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/443,389

(22) Filed: Jul. 26, 2021

(65) Prior Publication Data

US 2022/0024865 A1 Jan. 27, 2022

Related U.S. Application Data

(60) Provisional application No. 62/706,017, filed on Jul. 27, 2020.

(51) Int. Cl.
*C07C 303/34* (2006.01)
*C02F 1/68* (2023.01)
*C07C 211/04* (2006.01)

(52) U.S. Cl.
CPC ............ *C07C 303/34* (2013.01); *C02F 1/683* (2013.01); *C07C 211/04* (2013.01)

(58) Field of Classification Search
None
See application file for complete search history.

(56) References Cited

U.S. PATENT DOCUMENTS

2018/0186668 A1 7/2018 Nicholas et al.

OTHER PUBLICATIONS

Cai ("Significant contributions of trimethylamine to sulfuric acid nucleation in polluted environments" npj Climate and Atmospheric Science, 2023(6):75, p. 1-8; https://doi.org/10.1038/s41612-023-00405-3) (Year: 2023).*
Almeida ("Molecular understanding of sulphuric acid-amine particle nucleation in the atmosphere" Nature, 2013(502), p. 359) (Year: 2013).*

(Continued)

*Primary Examiner* — Amy C Bonaparte
(74) *Attorney, Agent, or Firm* — Kilpatrick Townsend & Stockton LLP

(57) ABSTRACT

Disclosed herein are clusters compounds that include at least one substituted amine sulfate and at least one substituted amine bisulfate molecule. The substituted amine sulfate molecule and the substituted amine bisulfate molecule may each include an ammonium moiety with at least one alkyl substituent. Optionally, the alkyl substituent can include 1 to 20 carbon atoms, 1 to 10 carbon atoms, or 1 to 6 carbon atoms. For example, the alkyl substituent can be a methyl, ethyl, propyl, butyl, or pentyl group. In some examples, the substituted amine sulfate molecule and the substituted amine bisulfate molecule each include an ammonium moiety with at least two alkyl substituents. Optionally, the two alkyl substituents are the same. Alternatively, however, the two alkyl substituents can be different.

45 Claims, 11 Drawing Sheets

(56) References Cited

OTHER PUBLICATIONS

Jen ("Stabilization of sulfuric acid dimers by ammonia, methylamine, dimethylamine, and trimethylamine" J. Geophys. Res. Atmos. 2014(119), p. 7502-7514; doi:10.1002/2014JD021592) (Year: 2014).*

Kurten ("Neutral molecular cluster formation of sulfuric acid-dimethylamine observed in real time under atmospheric conditions" PNAS 2014(111), p. 15019; www.pnas.org/cgi/doi/10.1073/pnas.1404853111) (Year: 2014).*

Yao ("Atmospheric new particle formation from sulfuric acid and amines in a Chinese megacity" Science, 2018(361), p. 278-2814) (Year: 2018).*

Jiang ("Sulfuric acid-amine nucleation in urban Beijing" Atmos. Chem. Phys. 2021(21), p. 2457-2468; https://doi.org/10.5194/acp-21-2457-2021) (Year: 2021).*

Yin ("The missing base molecules in atmospheric acid-base nucleation" National Science Review, 2022(9), p. 1-13; https://doi.org/10.1093/nsr/nwac137), (Year: 2022).*

Bzdek et al., "Size-Dependent Reactions of Ammonium Bisulfate Clusters with Dimethylamine", The Journal of Physical Chemistry A, vol. 114, No. 43, Oct. 11, 2010, pp. 11638-11644.

Khoma et al., "Onium Sulfates and Hydrogen Sulfates: Products of Reactions of Sulfur(IV) Oxide with Aqueous Solutions of Alkylamines and Aniline", Physical Methods of Investigation, Russian Journal of Inorganic Chemistry, vol. 63, No. 5, Jun. 7, 2018, pp. 655-660.

Kupiainen et al., "Amine Substitution Into Sulfuric Acid—Ammonia Clusters", Atmospheric Chemistry and Physics, vol. 12, Issue 8, Apr. 16, 2012, pp. 3591-3599.

International Application No. PCT/US2021/043180 , International Search Report and Written Opinion, Mailed On Nov. 5, 2021, 8 pages.

Anto et al., "FT-TR, FT-Ramen and SERS Spectra of Anilinium Sulfate", Journal of Raman Spectroscopy, vol. 40, No. 12, Jun. 1, 2009, pp. 1810-1815.

Chan et al., "Role of the Aerosol Phase in Ammonia/Amines Exchange Reactions", Environmental Science & Technology, vol. 47, No. 11, May 28, 2023, pp. 5755-5762.

EP21850505.5, "Extended European Search Report", Jul. 29, 2024, 8 pages.

Matulkova et al., "Semi-organic Salts of Aniline With Inorganic Acids: Prospective Materials for the Second Harmonic Generation", Crystengcomm, vol. 13, No. 12, Jan. 1, 2011, pp. 4131-4138.

* cited by examiner

CLUSTER COMPOUNDS AND METHODS OF MAKING THE SAME

CROSS-REFERENCE TO RELATED APPLICATIONS

The present application claims the benefit of U.S. Provisional Patent Application 62/706,017, filed Jul. 27, 2020, the entirety of which is hereby incorporated by reference.

TECHNICAL FIELD

The present disclosure relates to amine cluster compounds and more specifically to amine cluster compounds including substituted amine sulfate and substituted amine bisulfate.

BACKGROUND

Water treatment processes have been designed to improve the quality of water to make it more acceptable for a specific end use, such as drinking, industrial water supply, irrigation, river flow maintenance, water recreation or many other uses. Water treatment removes or reduces biological or chemical contaminants so that the water is acceptable for its desired use. Treatment for the production of drinking water involves the removal of contaminants from unprocessed water to produce water that is pure enough for human consumption without any short term or long term risk of any adverse health effect. In general terms, the greatest microbial risks are associated with ingestion of water that is contaminated with human or animal feces, which can be a source of pathogenic bacteria, viruses, protozoa and helminths. The destruction of microbial pathogens and/or heavy metals is essential and commonly involves the use of reactive chemical agents such as copper or chlorine, aeration, flocculation and polyelectrolytes. Other chemicals that have been adopted to make industrial water suitable for discharge include chemical coagulation, chemical precipitation, chemical disinfection, chemical oxidation, advanced oxidation, ion exchange, and chemical neutralization.

Base products such as chelating agents have been blended with copper sulfate for various uses in water-based treatment systems, such as the eradication and control of dreissenid mussels. However, these base products are difficult to produce safely. An early process utilized water, ammonia, and sulfuric acid to produce a novel acid and involved a vat mixing batch process where sulfuric acid was slowly mixed to an aqueous ammonium solution. This process was performed in open vats and was dangerous due to the extremely exothermic nature of the reactions involved. The process was often termed a "cold process" as the mixing was slowed down to avoid excess heat generation and/or explosions from occurring. There have been several attempts to improve upon the "cold process" such a vat mixing process involving the use of high pressure and high voltage DC current, however, the risk associated with these processes remains.

Therefore, there is a need for new base products that are safer to produce and can be combined with copper to create an effective water treatment formulation.

SUMMARY

A cluster compound disclosed herein includes a cluster of molecules including at least one substituted amine sulfate molecule and at least one substituted amine bisulfate molecule. In some examples, the substituted amine sulfate molecule and the substituted amine bisulfate molecule each include an ammonium moiety with at least one alkyl substituent. Optionally, the alkyl substituent can include 1 to 20 carbon atoms, 1 to 10 carbon atoms, or 1 to 6 carbon atoms. For example, the alkyl substituent can be a methyl, ethyl, propyl, butyl, or pentyl group. In some examples, the substituted amine sulfate molecule and the substituted amine bisulfate molecule each include an ammonium moiety with at least two alkyl substituents. Optionally, the two alkyl substituents are the same. Alternatively, however, the two alkyl substituents can be different. In some examples, in addition to or instead of at least one alkyl substituent, the ammonium moieties of the amine sulfate and the amine bisulfate each include at least one aryl substituent. Optionally, the aryl substituent includes 4 to 20 carbon atoms. The aryl substituent may further include one or more heteroatoms, such as sulfur, nitrogen, or oxygen. For example, when the aryl substituents includes only 4 carbon atoms, it should include one or more heteroatoms. Specific examples of the aryl substituent include but are not limited to substituted or unsubstituted phenyl, benzyl, napthyl, thiophene, furan, or pyrrole. In some examples, the substituted amine sulfate molecule and the substituted amine bisulfate molecule each comprise a secondary or tertiary ammonium. Optionally, a cluster compound described herein can further include at least one sulfuric acid molecule and/or at least one water molecule.

In some aspects, a cluster compound described herein includes Formula I:

$$((R_aNH_{4-a})_2SO_4)\cdot(R_aNH_{4-a}HSO_4)_n \qquad (I)$$

wherein each R independently is alkyl or aryl; a is 1, 2, or 3; and n is 1, 2, 3, 4, 5, 6, 7, 8, 9, 10 or more. Optionally, at least one R is methyl, and Formula I becomes Formula II:

$$(((CH_3)_aR_bNH_{(4-(a+b))})_2SO_4)\cdot((CH_3)_aR_bNH_{(4-(a+b))}HSO_4)_n \qquad (II)$$

wherein each R independently is alkyl or aryl; a is 1, 2, or 3; b is 0, 1, or 2, provided a+b is 1, 2, or 3; and n is 1, 2, 3, 4, 5, 6, 7, 8, 9, 10 or more. For example, when a is 1, b can be 0, 1, or 2; when a is 2, b can be 0 or 1; and when a is 3, b is 0. In some examples, the cluster compound further includes molecules of sulfuric acid and, optionally, molecules of water, and the cluster compound includes Formula III:

$$((R_aNH_{4-a})_2SO_4)_x\cdot(H_2SO_4)_y\cdot(H_2O)_z\cdot((R_aNH_{4-a})HSO_4)_n \qquad (III)$$

wherein each R independently is alkyl or aryl; a is 1, 2, or 3; x is at least 1, y can be zero, z can be zero, and n is at least one. Optionally, x is from 1 to 5, y is from 0 to 5, z is from 0 to 5, and n is 1, 2, 3, 4, 5, 6, 7, 8, 9 or 10, or n is from 1 to 20.

In any formula described herein, at least one R can be an alkyl substituent. For example, R can be an alkyl substituent including 1 to 20 carbon atoms, 1 to 10 carbon atoms, or 1 to 6 carbon atoms. In some examples, R is a methyl, ethyl, propyl, butyl, or pentyl group. Optionally, in any formula described herein, each R can be a methyl group. Alternatively, in any formula described herein, at least one R can be an aryl substituent. For example, at least one R can be an aryl substituent including from 4 to 20 carbon atom.

In some examples, a cluster compound described herein forms a solution having a pH below about 2. Optionally, the solution has a concentration of the cluster compounds of from about 10% to about 50% by weight in the solution.

Also described herein is a method of forming a cluster compound, the method including combining an amine and sulfuric acid to form a reaction mixture, wherein the amine and sulfuric acid are combined in water; and cooling the reaction mixture to form a product mixture that includes a cluster compound including at least one substituted amine sulfate molecule and at least one substituted amine bisulfate molecule. Optionally, combining the amine and the sulfuric acid is carried out without temperature control. In some examples, combining the amine and the sulfuric acid includes adding an aqueous solution of the amine to water containing the sulfuric acid. Optionally, the molar ratio of amine to sulfuric acid in the reaction mixture is about 2:1. Optionally, the amine includes at least one alkyl or one aryl substituent. In some examples, the alkyl substituent can include from 1 to 20 carbon atoms, from 1 to 10 carbon atoms, or from 1 to 6 carbon atoms. Optionally, the amine can be monomethyl amine, dimethyl amine, or trimethyl amine.

In some embodiments, the amine can include at least one aryl substituent. In some examples, the aryl substituent includes from 4 to 20 carbon atoms. The aryl substituent may further include one or more heteroatoms, such as sulfur, nitrogen, or oxygen. As one example, if the aryl substituent includes only 4 carbon atoms, then the aryl substituent has at least one heteroatom such as, for example nitrogen or sulfur. The aryl substituent may be substituted or unsubstituted. Specific examples of the aryl substituents include, but are not limited to, substituted or unsubstituted phenyl, benzyl, napthyl, thiophene, furan, or pyrrole. In some aspects, the cluster compound includes Formula I, wherein each R independently is alkyl or aryl; a is 1, 2, or 3; and n is 1, 2, 3, 4, 5, 6, 7, 8, 9, 10 or more.

In the method disclosed herein, optionally the amine/sulfuric acid reaction mixture described previously is a first reaction mixture, the amine/sulfuric acid product mixture described previously is a first product mixture, and the method further includes adding additional sulfuric acid to the first product mixture to form a second reaction mixture; and cooling the second reaction mixture to form a second product mixture that includes a second cluster compound including molecules of amine sulfate and amine bisulfate. Optionally, adding the additional sulfuric acid to the first product mixture is carried out without temperature control. In some examples, the molar ratio of amine to additional sulfuric acid in the second reaction mixture is from about 0.2 to about 0.6. For example, the molar ratio of amine to additional sulfuric acid in the second reaction mixture typically is about 0.4. In some aspects, the second cluster compound includes Formula III, wherein each R independently is alkyl or aryl; a is 1, 2, or 3; x is at least 1, y can be zero, z can be zero, and n is at least one.

Covered embodiments of the invention are defined by the claims, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

BRIEF DESCRIPTION OF THE FIGURES

Features and advantages of the compounds and methods described herein will be more fully appreciated by reference to the following detailed description of illustrative examples when taken in conjunction with the accompanying figures in which.

DETAILED DESCRIPTION

Figure 1:
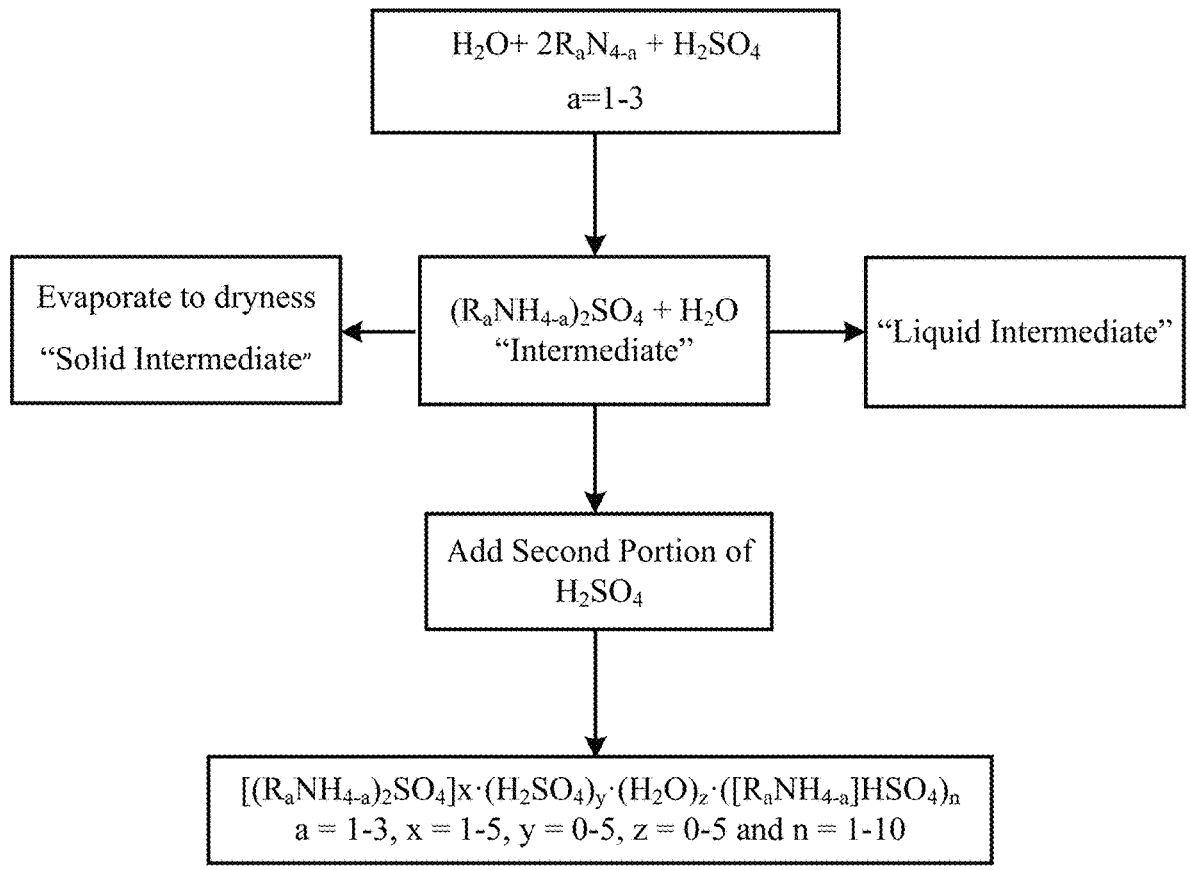
FIG. 1 is a flowchart depicting a synthetic route as described herein.

Disclosed herein are cluster compounds and methods of making the same. The cluster compounds include individual molecules of amine sulfate (substituted ammonium sulfate) and amine bisulfate (substituted ammonium bisulfate) aggregated together in a single structure. The cluster compounds have unusual properties. As one example, the cluster compounds are acidic and can be corrosive to metals yet simultaneously non-corrosive to human skin. These compounds are not chelates in the classical description of a chelate. These cluster compounds do not release a heat of formation with metals typical of a classical chelate. They provide an acid environment for metals to reside. Another aspect of this class of cluster compounds is to slowly release acid through a membrane.

Definitions and Descriptions

As used herein, the terms "invention," "the invention," "this invention," and "the present invention" are intended to refer broadly to all of the subject matter of this patent application and the claims below. Statements containing these terms should be understood not to limit the subject matter described herein or to limit the meaning or scope of the patent claims below.

As used herein, the meaning of "a," "an," or "the" includes singular and plural references unless the context clearly dictates otherwise.

As used herein, the meaning of "room temperature" includes any temperature of from about 15° C. to about 30° C., for example about 21° C. to about 26° C.

All ranges disclosed herein encompass both endpoints as well as any and all subranges subsumed therein. For example, a stated range of "1 to 10" includes any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

As used herein, the terms "cluster compound" or "molecular cluster compounds" refer to a discrete assembly of two or more individual molecules held together as a single aggregated structure. The individual molecules in the cluster may be held together by hydrogen bonding, Van der Waals forces, ionic forces, or a combination thereof.

As used herein, the term amine sulfate refers to a primary, secondary, or tertiary ammonium sulfate, and the term amine bisulfate refers to a primary, secondary, or tertiary ammonium bisulfate.

Cluster Compounds

Disclosed herein are cluster compounds, or molecular cluster compounds, that include molecules of at least one amine sulfate and at least one amine bisulfate. The cluster compounds described herein include amine sulfates and amine bisulfates formed from alkyl or aryl amines.

An alkyl amine is an amine that includes at least one alkyl substituent. In some examples, the alkyl substituent(s) have 1 to 20 carbon atoms, 1 to 10 carbon atoms, or 1 to 6 carbon atoms. In some examples, the alkyl substituent(s) are methyl, ethyl, propyl, butyl, or pentyl group(s). When the alkyl amine includes two or more alkyl substituents, the alkyl substituents may be the same or different.

An aryl amine is an amine that includes at least one aryl substituent. In some examples, the aryl substituent(s) have at least 4 carbon atoms. In some examples, the aryl substituent (s) have no more than 20 carbon atoms. Optionally, the aryl substituent(s) have 4 to 20 carbon atoms. In some examples, the aryl substituent further includes at least one heteroatom, such as nitrogen, sulfur, or oxygen. For example, if the number of carbon atoms is 4, then the aryl substituent has at least one heteroatom.

In some examples, a cluster compound described herein includes Formula I:

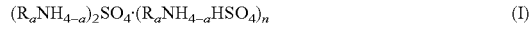
(R$_a$NH$_{4-a}$)$_2$SO$_4$·(R$_a$NH$_{4-a}$HSO$_4$)$_n$ (I)

where each R independently is alkyl or aryl; a is 1, 2, or 3; and n is 1, 2, 3, 4, 5, 6, 7, 8, 9, 10 or more. In some examples, the amine sulfate and amine bisulfate are formed from a primary ammonium (a=1), and the cluster compound includes Formula Ia.

(RNH$_3$)$_2$SO$_4$·(RNH$_3$HSO$_4$)$_n$ (Ia)

wherein R and n are defined as above for Formula I. In some examples, the amine sulfate and amine bisulfate are formed from a secondary ammonium (a=2), and the cluster compound includes Formula Ib.

(R$_2$NH$_2$)$_2$SO$_4$·(R$_2$NH$_2$HSO$_4$)$_n$ (Ib)

wherein R and n are defined as above for Formula I. In some examples, the amine sulfate and amine bisulfate are formed from a tertiary ammonium (a=3), and the cluster compound includes Formula Ic.

(R$_3$NH)$_2$SO$_4$·(R$_3$NHHSO$_4$)$_n$ (Ic)

wherein R and n are defined as above for Formula I.

In some embodiments, at least one R substituent is methyl, and a cluster compound described herein includes Formula II:

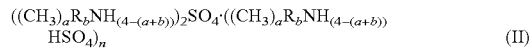
((CH$_3$)$_a$R$_b$NH$_{(4-(a+b))}$)$_2$SO$_4$·((CH$_3$)$_a$R$_b$NH$_{(4-(a+b))}$HSO$_4$)$_n$ (II)

where each R independently is alkyl or aryl; a is 1, 2, or 3; b is 0, 1, or 2, provided a+b is 1, 2, or 3; and n is 0, 1, 2, 3, 4, or 5. In some examples, each R in the cluster compound is methyl, b=0, and the cluster compound includes Formula IIa:

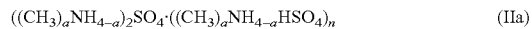
((CH$_3$)$_a$NH$_{4-a}$)$_2$SO$_4$·((CH$_3$)$_a$NH$_{4-a}$HSO$_4$)$_n$ (IIa)

where a and n are defined as above for Formula II.

Cluster compounds described herein may further include molecules of water and/or molecules of sulfuric acid aggregated with the molecules of amine sulfate and amine bisulfate. For these cluster compounds, Formula I becomes Formula III:

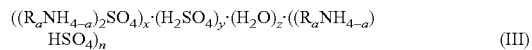
((R$_a$NH$_{4-a}$)$_2$SO$_4$)$_x$·(H$_2$SO$_4$)$_y$·(H$_2$O)$_z$·((R$_a$NH$_{4-a}$HSO$_4$)$_n$ (III)

where each R independently is alkyl or aryl; a is 1, 2, or 3; x is at least 1, y can be zero, z can be zero, and n is at least one. In some examples, x is from 1 to 5, y is from 0 to 5, z is from 0 to 5, and n is between 1 and 20.

In any formula described herein, each R independently can be alkyl or aryl. When any R is alkyl, that R can be methyl, ethyl, propyl, butyl, pentyl, C$_1$-C$_6$, C$_1$-C$_{10}$, or C$_1$-C$_{20}$. When any R is aryl, that R can include at least 4 carbon atoms, no more than 20 carbon atoms, or from 4 to 20 carbon atoms. In some examples, the aryl substituent includes at least one heteroatom, such as nitrogen, sulfur, or oxygen. For example, if the number of carbon atoms is 4, then the aryl substituent has at least one heteroatom. Specific examples of the aryl substituent include, but are not limited to, substituted or unsubstituted phenyl, benzyl, napthyl, thiophene, furan, or pyrrole. When more than one R is present, the R substituents can be the same or different. In some examples, at least one R substituent is alkyl and at least one other is aryl.

In various specific examples, a cluster compound described herein include s monomethylamine sulfate and monomethylamine bisulfate, dimethylamine sulfate and dimethylamine bisulfate, or trimethylamine sulfate and trimethylamine bisulfate. Optionally, a cluster compound described herein includes a combination of two or more of monomethylamine sulfate/bisulfate, dimethylamine sulfate/bisulfate, and trimethylamine sulfate/bisulfate.

In some aspects, a cluster compound described herein is an acidic compound that can be dissolved in water to form a solution that is corrosive to metals and simultaneously not corrosive to human skin. For example, a cluster compound described herein can be dissolved in water to form a solution of about 5-50% cluster compound, about 10-30% cluster compound, or about 20-25% cluster compound. In some examples, the cluster compound solutions have a pH of about 3 or less, a pH between about 0 and about 3, or a pH between about 1 and about 2. Surprisingly, even though the cluster compound forms a solution with a low pH, both the pure cluster compound and the low pH solution are non-corrosive to human skin. That is, when either the pure cluster compound or the low pH solution of cluster compound is placed on skin, no signs of reddening or irritation are felt or observed.

Methods of Making the Cluster Compounds

Also disclosed herein are methods of making the cluster compounds described herein. The methods herein include reacting an amine with sulfuric acid to provide a cluster compound. The reaction is carried out in water. Optionally, the cluster compound is further reacted with additional sulfuric acid to form a different cluster compound.

In some examples, the cluster compounds described herein are formed in water by combining, in water, sulfuric acid with an amine. The overall sulfuric acid and amine can be combined at a molar ratio of total sulfuric acid to amine of about 2.8 to about 1.0 (2.8:1). In some examples, the sulfuric acid to amine ratio is approximately 1:2 in the First Reaction. Preferably, the reaction is carried out under an inert atmosphere, such as under nitrogen. In some examples, the amine is added as a liquid. In other examples, the amine is added as a gas.

The reaction between the sulfuric acid and amine is exothermic, which can raise the temperature of the reaction mixture. In some embodiments, the reaction is allowed to proceed without any temperature control. In some embodiments, after the reaction mixture reaches a maximum temperature, the mixture is allowed to cool to room temperature. The reaction yields a cluster compound that includes a clustered combination of substituted amine sulfate molecules and amine bisulfate molecules. The product mixture can be used as-is, with the cluster compound dissolved in the aqueous product mixture, or the cluster compound can be recovered from the product mixture, such as by removing the aqueous solvent.

Other cluster compounds described herein can be formed by further reacting the cluster compound formed by the reaction described above. When necessary to distinguish the cluster compounds described herein, the cluster compounds formed by the reaction described above are referred to as intermediate cluster compounds and the compounds formed by further reacting the intermediate cluster compounds are referred to as final cluster compounds.

In some embodiments, a final cluster compound can be formed by treating an intermediate cluster compound with additional sulfuric acid to yield a final cluster compound including clustered molecules of amine sulfate and amine bisulfate. Preferably, the sulfuric acid added to the intermediate cluster compound to form the final cluster compound is added at a higher sulfuric acid to amine mole ratio than the sulfuric acid to amine mole ratio used to form the intermediate cluster compound. For example, the sulfuric acid to amine mole ratio used to form the final cluster compound can be 1.5:1 to 10:1. Note that this ratio describes the ratio of acid added to the intermediate to the moles of amine used to produce the intermediate. In some examples, the sulfuric acid to amine mole ratio is 2.3-1.

Similar to the reaction that forms the intermediate cluster compound, the reaction between the intermediate cluster compound and the additional sulfuric acid is exothermic, which can raise the temperature of the reaction mixture. Optionally, the reaction is allowed to proceed without any temperature control. In some embodiments, after the reaction mixture reaches a maximum temperature, the mixture is allowed to cool to room temperature. The reaction yields a cluster compound that includes a clustered combination of amine sulfate molecules and amine bisulfate molecules. The final product mixture can be used as-is, with the cluster compound dissolved in the aqueous final product mixture.

In some embodiments, a cluster compound described herein may include molecules of water and/or sulfuric acid in addition to the molecules of amine sulfate and amine bisulfate. Where an intermediate cluster compound includes the same type of molecules as a final cluster compound, the intermediate and final cluster compounds can have different ratios of the constituent molecules.

The amine moieties used in the reactions described above, can be mono-, di-, or tri-substituted. For example, monosubstituted amines would provide compounds of Formula Ia, set forth above; Formula II, where b is 0; or Formula III, where a is 1. Disubstituted amines would provide compounds of Formula Ib; Formula II, where b is 0; or Formula III, where a is 2. Trisubstituted amines would provide compounds of Formula Ic; Formula II, where b is 0; or Formula III, where a is 3.

An amine moiety used to form the cluster compounds described herein can be an alkyl or aryl amine. When the amine is an alkyl amine, in some examples the alkyl amine includes one or more alkyl substituents having 1 to 20 carbon atoms, 1 to 10 carbon atoms, or 1 to 6 carbon atoms. In some examples, the alkyl amine includes one or more methyl, ethyl, propyl, or butyl substituents. When the alkyl amine includes two or more alkyl substituents, the alkyl substituents may be the same or different. In various specific examples, the amine is a monomethyl amine, dimethyl amine, or trimethyl amine.

When the amine is an aryl amine, in some examples, the aryl amine includes at least one aryl substituent having at least 4 carbon atoms, no more than 20 carbon atoms, or 4 to 20 carbon atoms. In some examples, the aryl substituent includes at least one heteroatom, such as nitrogen, sulfur, or oxygen. If the number of carbon atoms is 4, then the aryl substituent must include at least one heteroatom. Specific examples of the aryl substituent include, but are not limited to, substituted or unsubstituted phenyl, benzyl, napthyl, thiophene, furan, or pyrrole.

When an amine described herein is substituted more than once, the substitutions can be the same or different. In some examples, at least one substituent may be alkyl and at least one other may be aryl.

Methods of Using the Cluster Compounds

The cluster compounds may be used to produce an end product for use in water-based treatment systems such as, but not limited to, swimming pools, wastewater lagoons, storage reservoirs, decorative fountains, cooling water, irrigation canals, ornamental lakes, ponds, lagoons, reservoirs, water features on golf courses, retention ponds, detention ponds, natural and artificial lakes, impoundments, estuaries, streams, and rivers, municipal and/or commercial water treatment systems, zebra mussel treatment systems, agricultural water treatment systems (e.g., control of tadpole shrimp), and irrigation lines (e.g., keeping drip irrigation lines open and free from algae and bacteria).

In certain embodiments, the cluster compounds are used to produce an end product that controls nuisance mollusks or bivalves such as zebra mussels and quagga mussels, crustaceans, and biofouling invertebrates. The end product may be formed by adding copper sulfate and water to the base product fluid. The end product may be placed at a location of a mollusk infestation or in an area to prevent mollusk infestation. In some embodiments, the end product is applied to open waters such as lakes, ponds, or reservoirs, to flowing waters such as pipelines, or to closed systems such as cooling systems or fire suppression systems. An effectiveness of the end product may depend on ambient water conditions such as, but not limited to, temperature, alkalinity, hardness, and total organic carbon (TOC).

For open water treatment, the end product may be applied directly to the body of water being treated. In some embodiments, the end product is applied at the water surface and allowed to disperse. Because of the high diffusion rate provided by the base product fluid, metal or metal salts may disperse readily in stagnant (static) water systems. In some embodiments, the end product is directed to a specific location (e.g., at or near a pipe input) via hoses, pumps, diffusers, etc.

For flowing water treatment, the end product may be provided continuously into or on the flowing water. The end product may be used as a curative measure when adult or juvenile mollusks already exist (for which a higher initial dose may be needed) or as a preventative measure to inhibit colonization. For closed systems, the end product may be applied directly into a source for water in the system (e.g., a source or supply tank or reservoir).

For the treatment of mussels, the end product may be provided to the water system at a "lethal concentration" (e.g., a concentration that provides about 100% mortality of the mussels in a given time period).

In some embodiments, the base product fluid is used to produce an end product that is used to remove taste and odor compounds and/or microorganisms from drinking water (e.g., municipal drinking water). A common result of algae blooms in water, which may be eventually used for drinking water, is the formation of two compounds: geosmin and methyl iso-borneol (MIB). Geosmin and MIB, at concentrations in the ppt (parts per trillion) range may give water an objectionable earthy taste and/or odor. Current treatment options for taste and odor include high chlorine dosage, which is problematic in that carcinogenic chlorine byproducts are formed, and powder activated carbon, which may be expensive.

The treatment of water for taste and/or odor using the end product may not involve a mechanism utilising the copper in the end product. Removal of taste and/or odor from the water may be due to UV absorbing compounds found in the base product fluid and thus, the end product. In some embodiments, the end product is provided at a dose level of 1 ppm, which results in a copper equivalent level of about 57 ppb. Other dose levels may be used as desired and/or the end product may have a different (e.g., lower) concentration of copper as desired.

In some embodiments, the base product fluid is used to produce an end product for control and/or elimination of microorganisms in water systems. For example, the end product may be used to control and/or eliminate microorganisms in heat exchangers, metalworking fluids, reverse osmosis water processing, oil and gas field injection, fracturing, produced water, oil, and gas from wells and reservoirs, deaeration tower, oil and gas operation and transportation systems, oil and gas separation systems and storage tanks, oil and gas pipelines, gas vessels, toilet bowls, swimming pools, household drains, household surfaces, process equipment, sewage systems, wastewater and treatment systems, other industrial process water, boiler systems, ballast water and equipment, pipes, tubes, and other surfaces in these systems.

In some embodiments, the base product fluid is used to produce an end product that is used as a mosquito killer (e.g., "mosquito-cide"). Copper sulfate is known to kill mosquitoes. However, achieving an effective dose of copper (II) ions for killing mosquitoes may require a significant amount of copper sulfate and most of the copper sulfate (about 90%) may end up in a non-reactive solid as sludge on the bottom of the lake or water reservoir. In some embodiments, the base product fluid is used to produce an end product that potentially could be used as swimming pool sanitizer. Chlorine is the most widely used sanitizer for swimming pools. The only EPA recognized sanitizer other than chlorine is a system that uses biguanides and is sold under the trade name BACQUACIL®. There are currently no copper based products that have shown the efficacy to be approved by the EPA for use as a swimming pool sanitizer. In some embodiments, the end product is dosed into a swimming pool at levels to maintain the copper concentration between about 0.25 ppm and about 1.0 ppm. In some embodiments, the end product is formed from a solid (or powdered) base product mixed with a copper sulfate powder. The solid base product and copper sulfate mix may be formed into a solid shape or delivered using a metered delivery system into the swimming pool. The solid base product and copper sulfate mix may activate (rehydrate) when added to the swimming pool water.

In some embodiments, the base product fluid is used to produce an end product that is used as an algaecide. Copper may be used as a primary active ingredient against algae. There are certain species of algae, however, that do not respond well to copper alone. For example, black algae may not be well controlled with a copper based product alone. In some embodiments, the end product includes the addition of different metals other than copper to target specific algae strains and/or provide a broad spectrum product. For example, metals such as, but not limited to, silver or zinc may be added to the end product in addition to copper or in place of the copper.

In some embodiments, the base product fluid is used to produce an end product that is used for micronutrient delivery (e.g., an agriculture treatment solution used to increase the nutritional value of agricultural crops). The base product fluid may have improved chelating properties including holding the metal or metal salts in solution while also providing uptake of the metal or metal salts to plants or crops. Because of these improved properties, the base product fluid may be used in agriculture treatment solution formulations with compositions similar to those found in the market for traditional chelates such as EDTA. For example, one agriculture treatment solution formulation may include an end product that is a 9% zinc solution with the base product fluid. The formulation may be used as a foliarly applied micronutrient and may be applied at a rate of approximately one to two quarts per acre to crops such as corn, soybeans, and rice. Foliar application methods include mixing with pesticides and spraying it aerially, adding to the irrigation water in traditional pivot irrigators, or applying directly as a dilute water solution or mixing with pesticides through truck mounted spray units. In some embodiments, the end product includes a mixture containing zinc, magnesium, manganese, selenium, molybdenum, boron, iron, cobalt, copper, bismuth, or combinations thereof to supply a broad spectrum micronutrient application. The broad spectrum micronutrient application may be applied to agricultural crops such as corn and soybeans, which are typically treated with one or more metals complexed with EDTA. The end product for micronutrient delivery may provide a higher micronutrient uptake than EDTA due to the improved chelating properties of the base product fluid.

In some embodiments, the base product fluid is used to produce an end product that is used as an adjuvant to move or be moved (e.g., via cellular membrane transport systems) compounds across cell membranes. For example, a herbicide used with agricultural crops may include the base product fluid to increase the efficacy of the herbicide. In some embodiments, the end product is to increase the efficiency for fertilization of plants or crops.

In some embodiments, the base product fluid is used to produce an end product that is used for potable water treatment. In some embodiments, the base product fluid is used to produce an end product that is used to remove bacteria and/or cyanobacteria from water-based systems. In some embodiments, the end product is used to help pretreat algae, organics, bacteria, and/or cyanobacteria in a water source. New EPA rules are mandating that surface water treatment plants reduce their use of chlorine in order to reduce disinfection by products. The end product may provide enhanced anti-microbial properties due to more rapid penetration through cell walls. Thus, in some embodiments, the end product may be used to maintain bacterial control of the water prior to going into the public distribution system by removing *E. coli, cryptosporidium*, and giardia at lower concentrations. *E. coli* and other bacterial species may exist as cells in the water matrix (e.g., planktonic cells) or attached to a surface where they may form a complex layer referred to as a biofilm. When attached to the surface as the biofilm, bacterial species are typically less susceptible to chlorine and other antimicrobial agents. Due to the chemical nature of the end product described herein, it is anticipated that planktonic cells and those in biofilms may be susceptible to the end product's antimicrobial action. The use of the end product may reduce chlorine dose rates and assist in compliance with new EPA rules. Additionally, the end product may improve the economics of treatment compared to current treatments using chlorine.

In some embodiments, the base product fluid is used to produce an end product that is used as a fungicide. For example, the end product may be used for fungal control on plants in greenhouses, fields, and residential and commercial locations. In some embodiments, the base product fluid is used to produce an end product that is used for treatment of water used in shellfish depuration processes and/or treatment of water used in aquaculture facilities to inhibit odors and to control cyanobacteria (e.g., toxin producers). In some embodiments, the base product fluid is used to produce an end product that is used as an adjuvant to move compounds across cell membranes. In some embodiments, the base product fluid is used to produce an end product that is used in a cold cream product or other facial or beauty products. For example, the end product may be used for topical treatment of skin wounds, ulcers, or other external infections.

While the above embodiments describe a process for making a base product fluid using sulfuric acid and the uses of the sulfuric acid-based, base product fluid, in some embodiments, other acids may be used instead of or in combination with sulfuric acid to produce an alternative base product fluid. The alternative base product fluid may have different structures and/or different properties depending on the combination of acids used to make the base product fluid. Examples of acids that may be used include, but are not limited to, phosphoric acid ($H_3PO_4$), hydrochloric acid (HCl), and nitric acid ($HNO_3$). Additional acids that may be used include, but are not limited to, variations or derivatives of phosphoric acid such as polyphosphoric acid and phosphorous pentoxide ($P_2O_5$) and/or other hydrogen halides such as hydrofluoric acid fluoride, hydrobromic acid, or hydroiodic acid (in addition to their anhydrides). Acids, especially hydrogen halides, may be provided in either liquid or gaseous form.

In some embodiments, the alternative acid is used in combination with sulfuric acid. For example, the alternative acid may be used as the second portion of acid added to the intermediate of the base product fluid instead of sulfuric acid. The second portion of alternative acid may be added to the intermediate with the intermediate formed by sulfuric acid being in either reaction solution (e.g., fluid form) or in solid form. In embodiments with phosphoric acid added as the second portion of acid to the intermediate of the base product fluid, the resultant alternative base product fluid may include a mix of sulfuric acid and phosphoric acid ammonium based compounds. In embodiments with hydrochloric acid (or other hydrogen halides) added as the second portion of acid, the resultant alternative base product fluid may include a mix of sulfuric acid and hydrochloric acid ammonium based compounds. In embodiments with nitric acid added as the second portion of acid, the resultant alternative base product fluid may include a mix of sulfuric acid and nitric acid ammonium based compounds.

In some embodiments, the alternative acid is used instead of sulfuric acid throughout the process. For example, the alternative acid may be used as the acid reacted with the amine and water as well as the acid added to the (new) intermediate of the base product fluid. The resultant alternative base product fluid may include a cluster of ammonium salts, the alternative acid, and water. The ammonium salts may include, for example, one or more ammonium salts derived from the alternative acid. In embodiments with phosphoric acid as the acid, the resultant alternative base product fluid may include clusters of ammonium and phosphoric acid based compounds. In embodiments with hydrochloric acid (or other hydrogen halides) as the acid, the resultant alternative base product fluid may include clusters of ammonium and hydrochloric acid based compounds. In embodiments with nitric acid added as the acid, the resultant alternative base product fluid may include clusters of ammonium and nitric acid based compounds.

The following examples will serve to further illustrate the present invention without, however, constituting any limitation thereof. On the contrary, it is to be clearly understood that resort may be had to various embodiments, modifications, and equivalents thereof which, after reading the description herein, may suggest themselves to those skilled in the art without departing from the spirit of the invention.

EXAMPLES

The synthesis and characterization of cluster compounds containing various amine groups are described herein. In each example, the amine (e.g., monomethyl amine, dimethyl amine, or trimethyl amine) was provided by Sigma-Aldrich (St. Louis, MO) and was used without purification. Monomethyl amine was a 40% solution in water, dimethyl amine was a 40% solution in water, and trimethyl amine was a 45% solution in water. Sulfuric acid was provided by Chemtrade Refinery Services, Inc. (Lawrence, KS) and was technical grade, 93% by weight. The water used in the experiments was distilled water.

Infrared spectrum were recorded on a Nicolet 1550-FT-IR spectrophotometer with a Smart iTR for solid and liquid samples. For the liquid samples the solvent was water, and the signal due to the water was subtracted out using Omnic 9 software. The mass spectral analysis was conducted using an Agilent 6220A time-of-flight (TOF) mass spectrometer equipped with an electrospray ionization (ESI) source. Each sample was injected as prepared and analyzed in both positive and negative ion mode (V mode). Source parameters were as follows: Positive ion mode, Capillary 0.1-1 kV, Sampling cone 74 V, Extraction cone 3.6 V and Ion Guide 2.5 V.

Example 1: Cluster Compounds with Monomethyl Amine

A three-neck flask equipped with a condenser, thermometer, and an addition funnel was charged with distilled water (20.76 grams) and 93% sulfuric acid (4.99 grams (total), 0.047 moles (as 100% sulfuric acid)). This mixture was stirred with a magnetic stir bar. The mixture was placed under nitrogen and was treated with a 40% aqueous solution of monomethyl amine (7.37 grams (total), 0.0949 moles (amine)). Upon treatment with the amine, the temperature increased from 30° C. to 68° C. The resulting mixture was allowed to cool to room temperature (about 21° C.) to form an intermediate aqueous product. The intermediate aqueous product had a density of 1.100 grams/ml and a pH of 2.64. A flowchart depicting a synthetic route of making the cluster compounds is shown in FIG. 1.

A small portion (1.13 grams) of the intermediate aqueous product was removed for analysis by electrospray mass spectrometry (ESI-MS) and infrared spectroscopy (IR). A second portion (10.02 grams) of the intermediate aqueous product was removed and heated to 90-95° C. under nitrogen to remove most of the liquid, leaving a white particulate intermediate solid product. The intermediate solid product was dried to a constant weight of 2.27 grams and analyzed by infrared spectroscopy.

Figure 2:
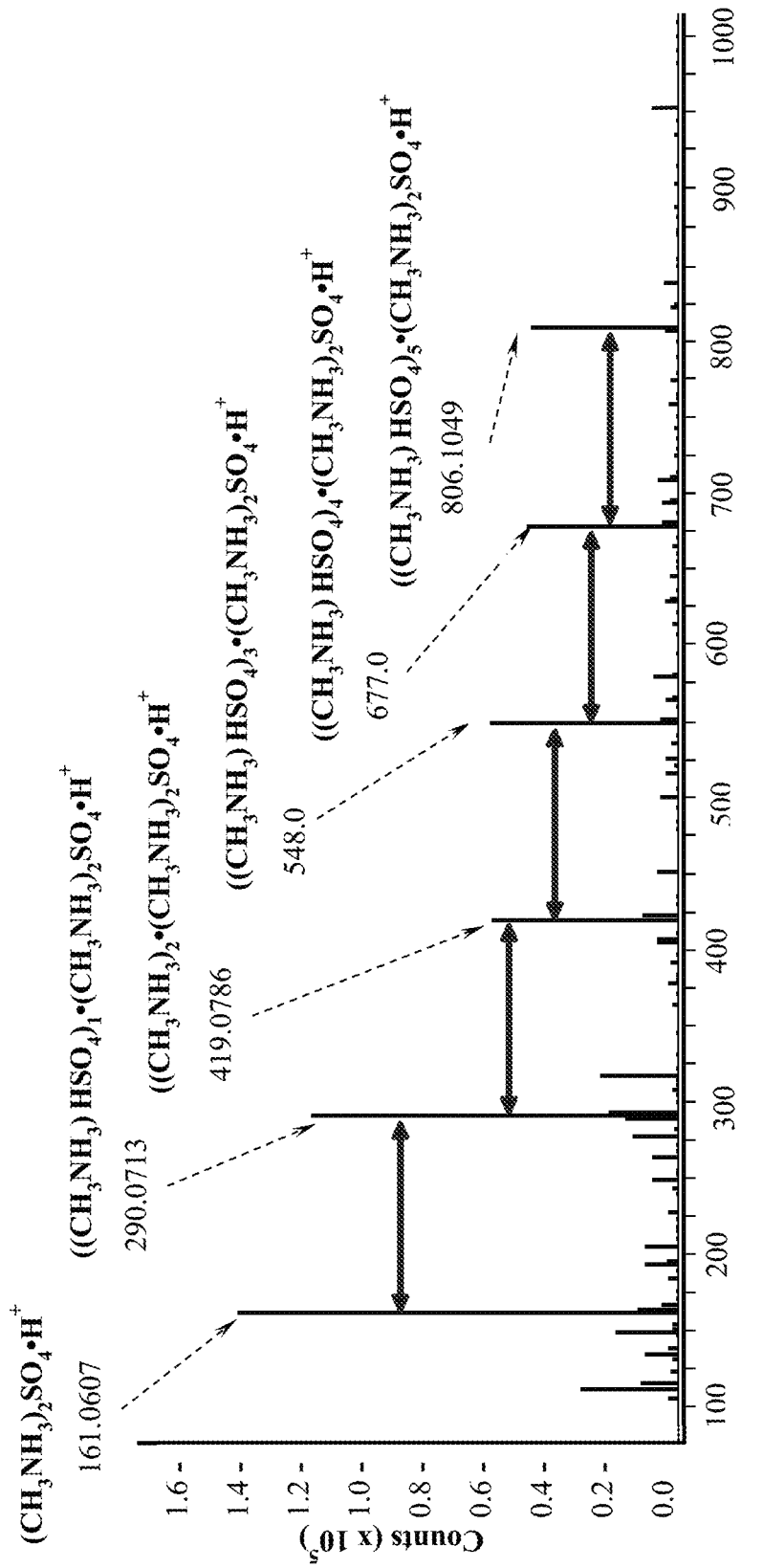
FIG. 2 is an electrospray ionization mass spectrometry (ESI-MS) spectrum of one example of a cluster compound as described herein, $R=CH_3$, a=1, b=0.

FIG. 2 is an electrospray mass spectrum of the monomethyl amine intermediate aqueous product. The spectrum includes major peaks at m/z=161, 290, 419, 548, 677, and 806. The peak at m/z=161 is consistent with protonated monomethyl amine sulfate, $((CH_3NH_3)_2SO_4) \cdot H^+$. The separation between adjacent major peaks is equal to the mass of monomethyl amine bisulfate, $CH_3NH_3HSO_4$. Thus, the spectrum is consistent with an intermediate aqueous product including cluster compounds having the formula $(CH_3NH_3)_2SO_4 \cdot (CH_3NH_4HSO_4)_n$, where n=0 to 5.

Figure 3:
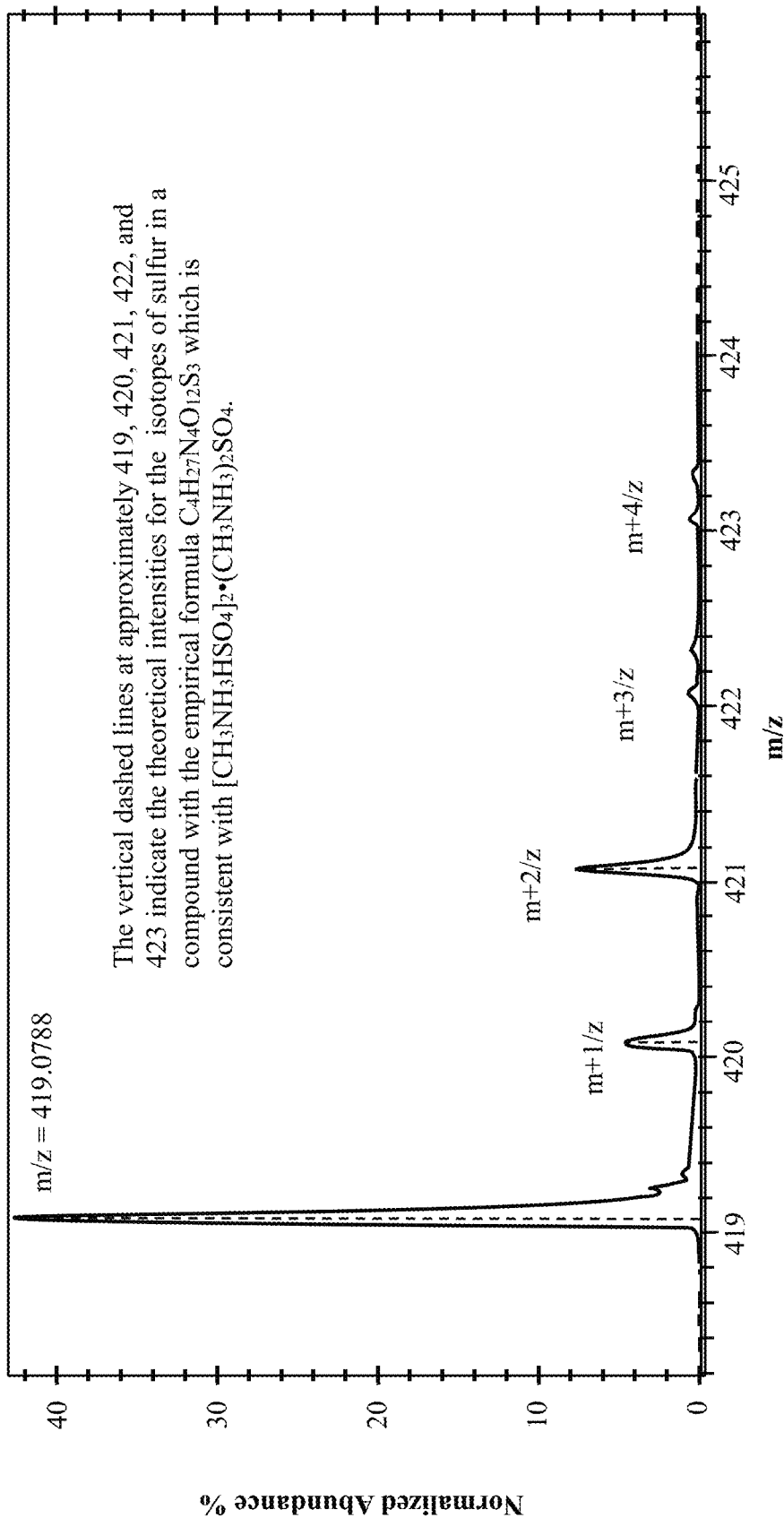
FIG. 3 is an expanded view of the High Resolution Mass spectrum shown in FIG. 2 from about m/z=418 to about m/z=426, showing the Isotopes of Sulfur.

FIG. 3 is an expanded portion of the ESI-MS spectrum shown in FIG. 2 from about m/z=418 to about m/z=426. FIG. 3 indicates three sulfur atoms in the compound represented by the molecular ion peak, M (m/z=419.0786), and the isotope peaks M+1 (m/z=420.1), M+2 (m/z=421.1), M+3 (m/z=422.1) and M+4 (m/z=423.1). The vertical lines inside the spectrum peaks indicate the theoretical intensities for the isotopes of sulfur ($^{33}S$ and $^{34}S$) in a compound with the molecular formula $(CH_3NH_3HSO_4)_2 \cdot (CH_3NH_3)_2SO_4$, which is consistent with the empirical formula $C_4H_{27}N_4O_{12}S_3$. The measured intensities are consistent with the theoretical intensities, so the spectrum is consistent with the empirical formula, indicating a compound with three sulfur atoms.

Figure 4:
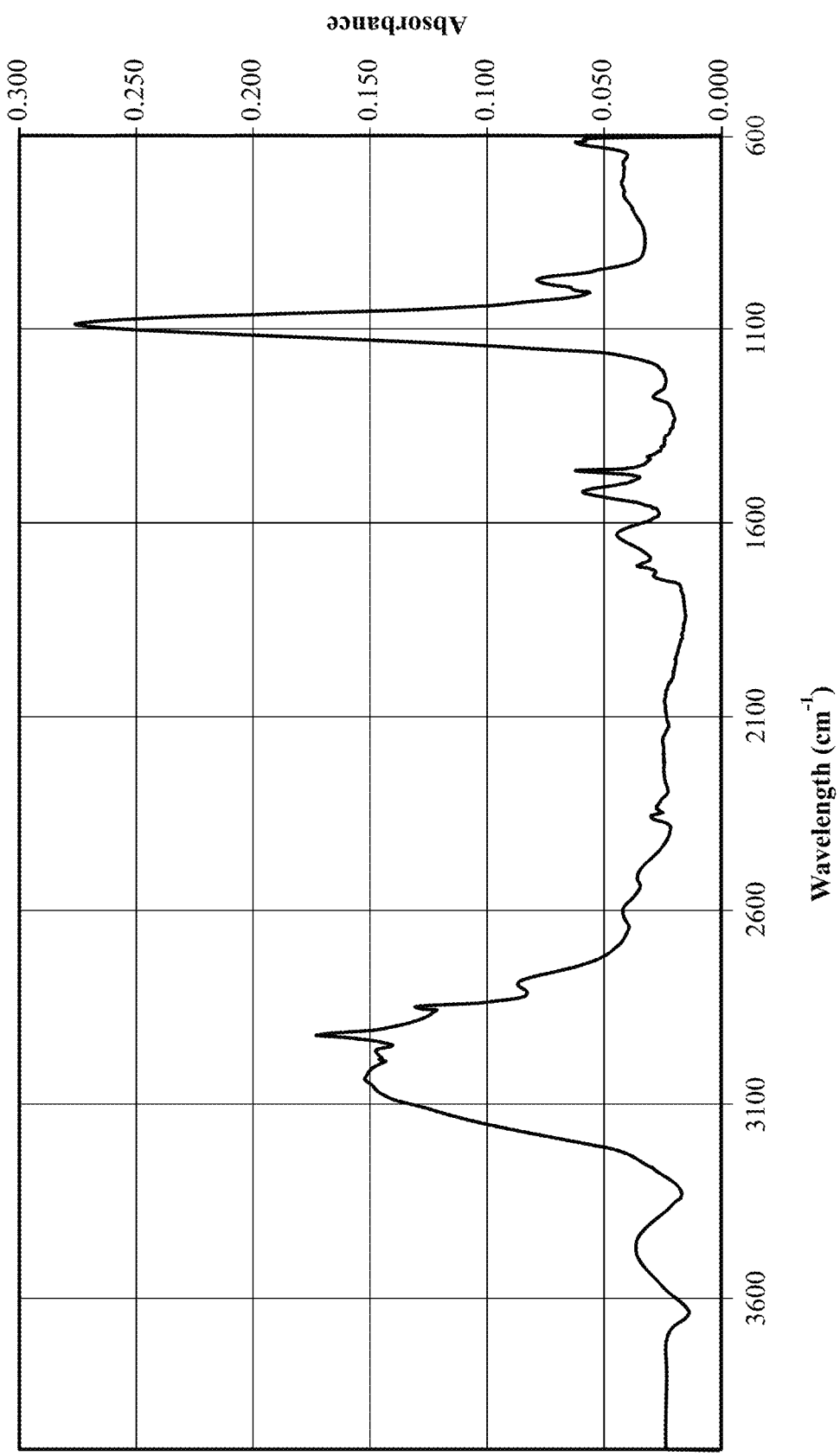
FIG. 4 is an infrared spectroscopy (IR) spectrum of one example of a cluster compound as described herein after first acid addition, $R=CH_3$, a=1, b=0.
Figure 5:
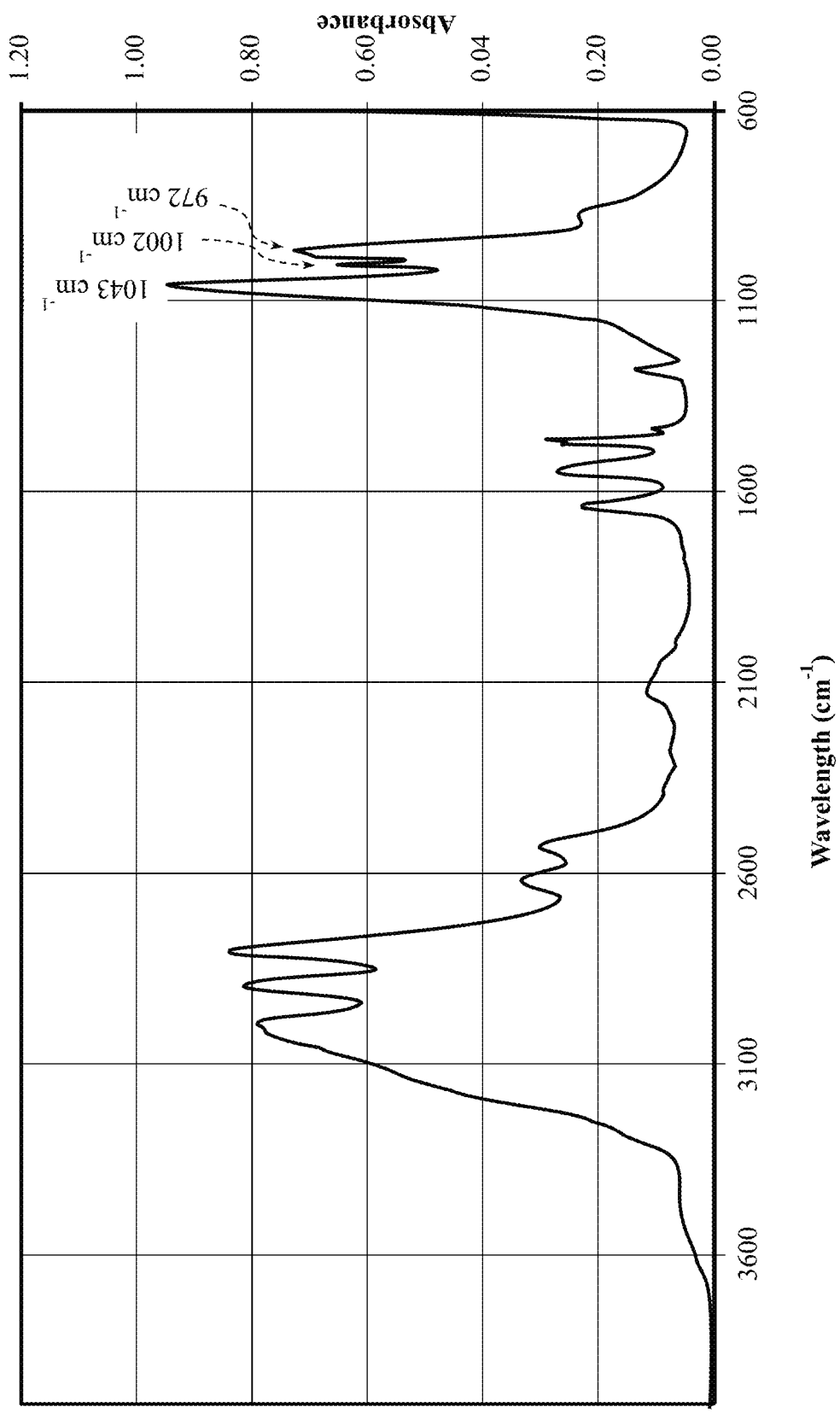
FIG. 5 is an IR spectrum of one example of a cluster compound after first acid addition as described herein as a solid, $R=CH_3$, a=1, b=0.

FIG. 4 is an IR spectrum of the intermediate aqueous product, and FIG. 5 is an IR spectrum of the intermediate solid product. In FIG. 4, the peaks at 3400 and 1467 cm$^{-1}$ are consistent with N—H stretching, and the peak at 1100 cm$^{-1}$ is consistent with a sulfate S=O stretching. In FIG. 5, the peaks at 3400 and 1620 cm$^{-1}$ are consistent with N—H stretching, and the peaks from 972 to 1043 cm$^{-1}$ are consistent with a bisulfate S=O stretching.

The ESI-MS analysis of the intermediate aqueous product and the IR analysis of the intermediate aqueous and solid products confirm the presence of molecular cluster compounds having the formula $(CH_3NH_3)_2SO_4 \cdot (CH_3NH_4HSO_4)_n$, where n=0 to 5.

21.23 grams of the intermediate aqueous product was maintained under nitrogen atmosphere and was treated with 93% sulfuric acid (14.88 grams (total), 0.141 moles (100% sulfuric acid)). Upon treatment with the sulfuric acid, the temperature increased from 22° C. to 61° C. The resulting mixture was allowed to cool to room temperature (about 21° C.) to form a final aqueous product. The density of the final aqueous product was 1.336 grams/ml. The observed sulfate concentration of the final aqueous product was 604,750 mg/L and the theoretical sulfate concentration was 616,446 mg/L. The final aqueous product was diluted 50 to 1, and the pH of the diluted final aqueous product was measured to be 1.23.

Example 2: Cluster Compounds with Dimethyl Amine

The reactions described in Example 1 were repeated with dimethyl amine instead of monomethyl amine using the same relative molar amounts of reactants. A three-neck flask equipped with a condenser, thermometer, and an addition funnel was charged with distilled water (18.76 grams) and 93% sulfuric acid (5.01 grams (total), 0.0475 moles (100% sulfuric acid)). This mixture was stirred with a magnetic stir bar. The mixture was placed under nitrogen and was treated with a 40% aqueous solution of dimethyl amine (10.71 grams (total), 0.095 moles (amine)). Upon treatment with the amine, the temperature increased from 31° C. to 67° C. The resulting mixture was allowed to cool to room temperature about 21° C. to form an intermediate aqueous product. The intermediate aqueous product had a density of 1.090 grams/ml and a pH of 2.55.

A small portion (2.17 grams) of the intermediate aqueous product was removed for analysis by electrospray mass spectrometry (ESI-MS) and infrared spectroscopy (IR). A second portion (10.02 grams) of the intermediate aqueous product was removed and heated to 90-95° C. under nitrogen to remove most of the liquid, leaving thick yellow oil. The intermediate yellow oil was heated (~40 C) under vacuum to a constant weight of 2.54 grams and analyzed by infrared spectroscopy.

The dimethyl amine and sulfuric acid were combined in water under nitrogen atmosphere at a mole ratio of 1:2 sulfuric acid to amine. The temperature increased as the reactants were combined, and the mixture was allowed to cool to room temperature to form an intermediate aqueous product.

As in Example 1, a portion of the dimethyl amine intermediate aqueous product was subjected to analysis by ESI-MS and IR. Another portion of the intermediate aqueous product was evaporated to constant weight, but the product was a thick oil which did not solidify and was not analyzed further.

Figure 6:
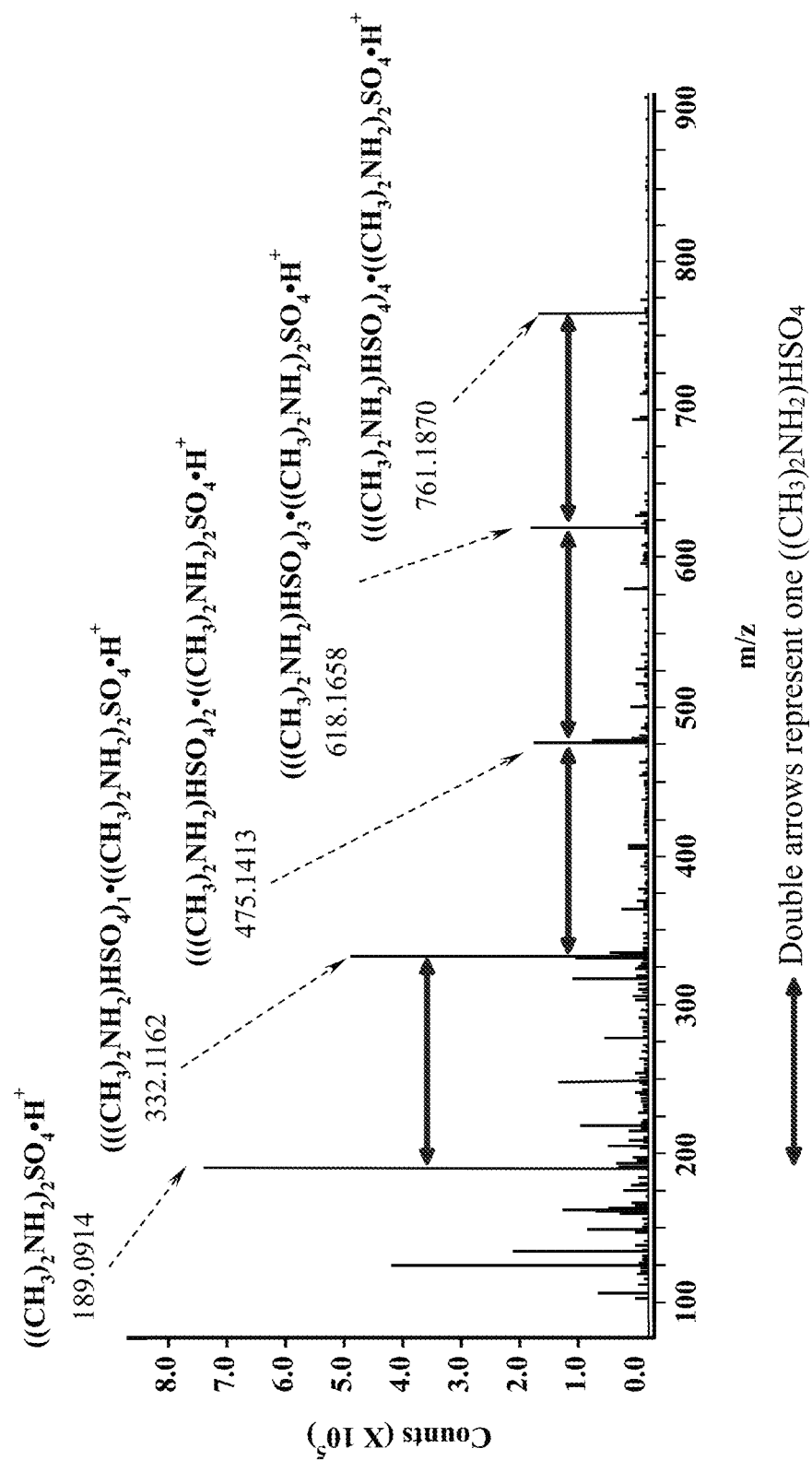
FIG. 6 is an ESI-MS spectrum of one example of a cluster compound as described herein, $R=CH_3$, a=2, b=0.

FIG. 6 is an ESI-MS spectrum of the dimethyl amine intermediate aqueous product. The spectrum includes major peaks at about m/z=189, 332, 475, 618 and 761. The peak at about m/z=189 is consistent with protonated dimethyl amine sulfate, $((CH_3)_2NH_2)_2SO_4 \cdot H^+$. The separation between adjacent major peaks is equal to the mass of dimethyl amine bisulfate, $(CH_3)_2NH_2HSO_4$. Thus, the spectrum is consistent with an intermediate aqueous product including cluster compounds having the formula $((CH_3)_2NH_2)_2SO_4 \cdot ((CH_3)_2NH_2HSO_4)_n$, where n=0 to 4.

Figure 7:
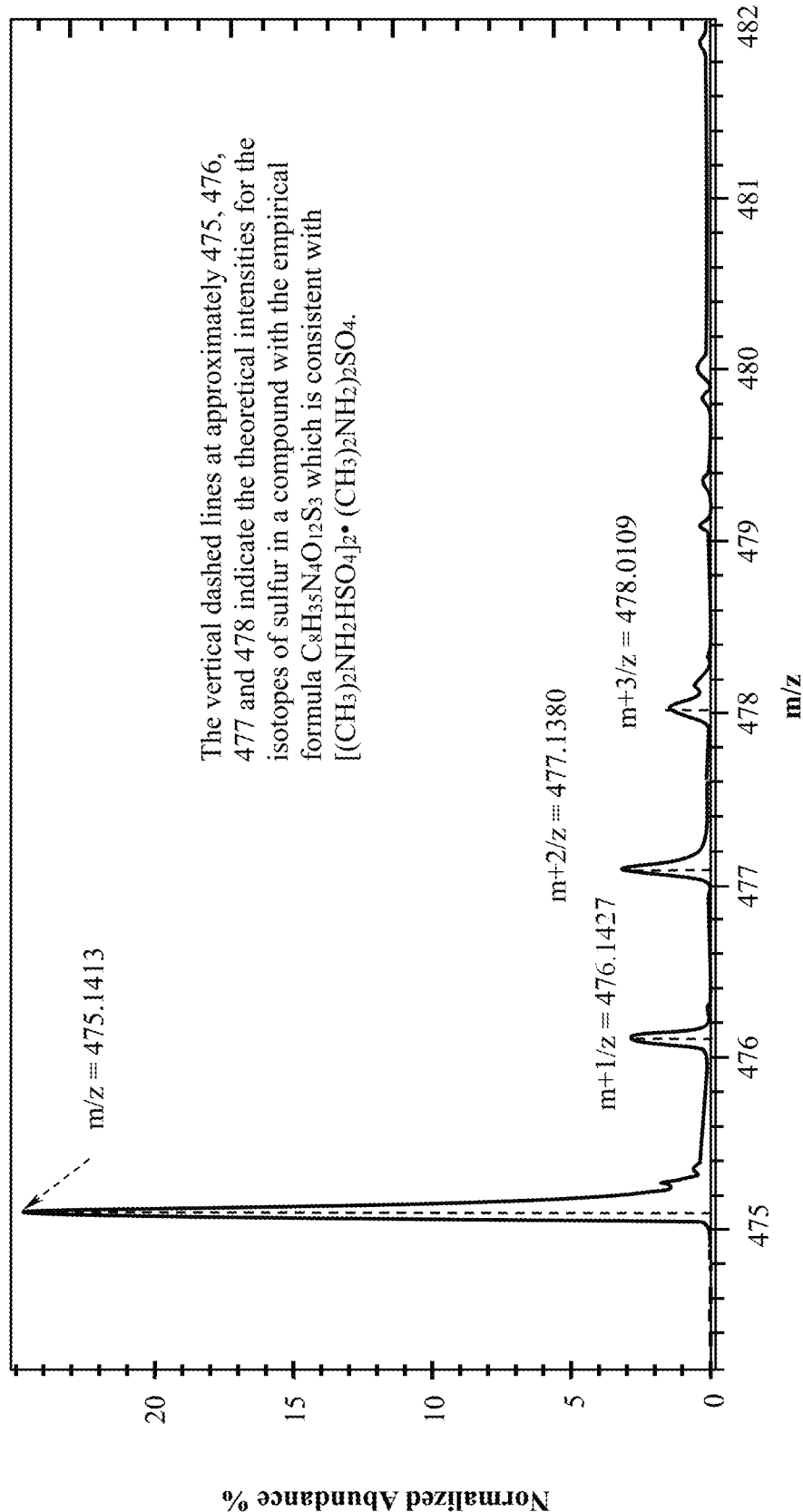
FIG. 7 is an expanded view of the High Resolution Mass spectrum shown in FIG. 6 from about m/z=474 to about m/z=482, showing the Isotopes of Sulfur, $R=CH_3$, a=2, b=0.

FIG. 7 is an expanded portion of the ESI-MS spectrum shown in FIG. 6 from about m/z=474 to about m/z=482. FIG. 7 indicates three sulfur atoms in the compound that is represented by the molecular ion peak, M (m/z=475.1413), and the isotope peaks M+1 (m/z=476.1427), M+2 (m/z=477.1380), and M+3 (m/z=478.0109). The vertical lines inside the spectrum peaks indicate the theoretical intensities for the isotopes of sulfur ($^{33}S$ and $^{34}S$) in a compound with the molecular formula $((CH_3)_2NH_2HSO_4)_2 \cdot ((CH_3)_2NH_2)_2SO_4$, which is consistent with the empirical formula $C_8H_{35}N_4O_{12}S_3$. The measured intensities are consistent with the theoretical intensities, so the spectrum is consistent with the empirical formula, indicating a compound with three sulfur atoms.

Figure 8:
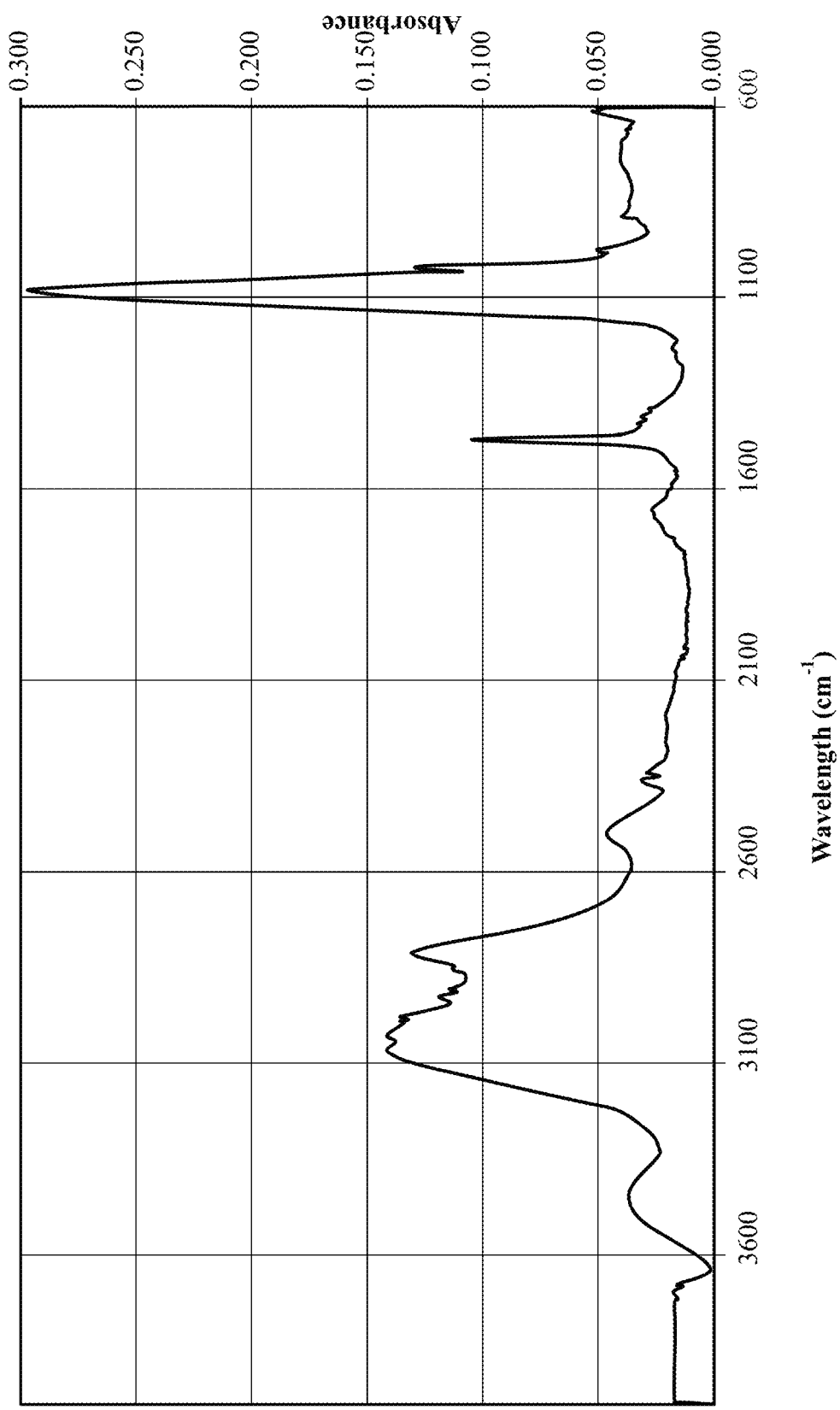
FIG. 8 is an IR spectrum of one example of a cluster compound as described herein after first acid addition, $R=CH_3$, a=2, b=0.

FIG. 8 is an IR spectrum of the dimethyl amine intermediate aqueous product. In FIG. 8, the peaks at 3400 and 1471 $cm^{-1}$ are consistent with N—H stretching and the peak at 1076 $cm^{-1}$ is consistent with a sulfate S=O stretching.

The ESI-MS and IR analyses of the dimethyl amine intermediate aqueous product confirm the presence of molecular cluster compounds having the formula $((CH_3)_2NH_2)_2SO_4\cdot((CH_3)_2NH_2HSO_4)_n$, where n=0 to 4.

As in Example 1, the remainder of the dimethyl amine intermediate aqueous product was treated with a second portion of sulfuric acid. As in Example 1, the mole ratio of the second portion of sulfuric acid to amine was 4.69-1.

The density of the final aqueous product was 1.306 grams/ml. The observed sulfate concentration of the final aqueous product was 570,375 mg/L and the theoretical sulfate concentration was 575,730 mg/L. The final aqueous product was diluted 50 to 1, and the pH of the diluted final aqueous product was measured to be 1.10.

Example 3: Cluster Compounds with Trimethyl Amine

The reactions described in Example 1 were repeated with trimethyl amine instead of monomethyl amine using the same relative molar amounts of reactants.

A three-neck flask equipped with a condenser, thermometer, and an addition funnel was charged with distilled water (18.26 grams) and 93% sulfuric acid (5.04 grams (total), 0.0475 moles (100% sulfuric acid)). This mixture was stirred with a magnetic stir bar. The mixture was placed under nitrogen and was treated with a 45% aqueous solution of trimethyl amine (12.46 grams (total), 0.095 moles (amine)). Upon treatment with the amine, the temperature increased from 33° C. to 60° C. The resulting mixture was allowed to cool to room temperature about 21° C. to form an intermediate aqueous product. The intermediate aqueous product had a density of 1.066 grams/ml and a pH of 2.68.

A small portion (1.83 grams) of the intermediate aqueous product was removed for analysis by electrospray mass spectrometry (ESI-MS) and infrared spectroscopy (IR). A second portion (10.02 grams) of the intermediate aqueous product was removed and heated to 90-95° C. under nitrogen to remove most of the liquid, leaving thick yellow oil. The intermediate yellow oil was heated (~40 C) under vacuum to a constant weight of 2.51 grams and analyzed by infrared spectroscopy.

The trimethyl amine and sulfuric acid were combined in water under nitrogen atmosphere at a mole ratio of 2:1 amine to sulfuric acid. The temperature increased as the reactants were combined, and the mixture was allowed to cool to room temperature to form an intermediate aqueous product.

As in Example 1, a portion (1.83 grams) of the trimethyl amine intermediate aqueous product was subjected to analysis by ESI-MS and IR. Another portion of the intermediate aqueous product was evaporated to constant weight, but the product was a thick oil which did not solidify and was not analyzed further.

Figure 9:
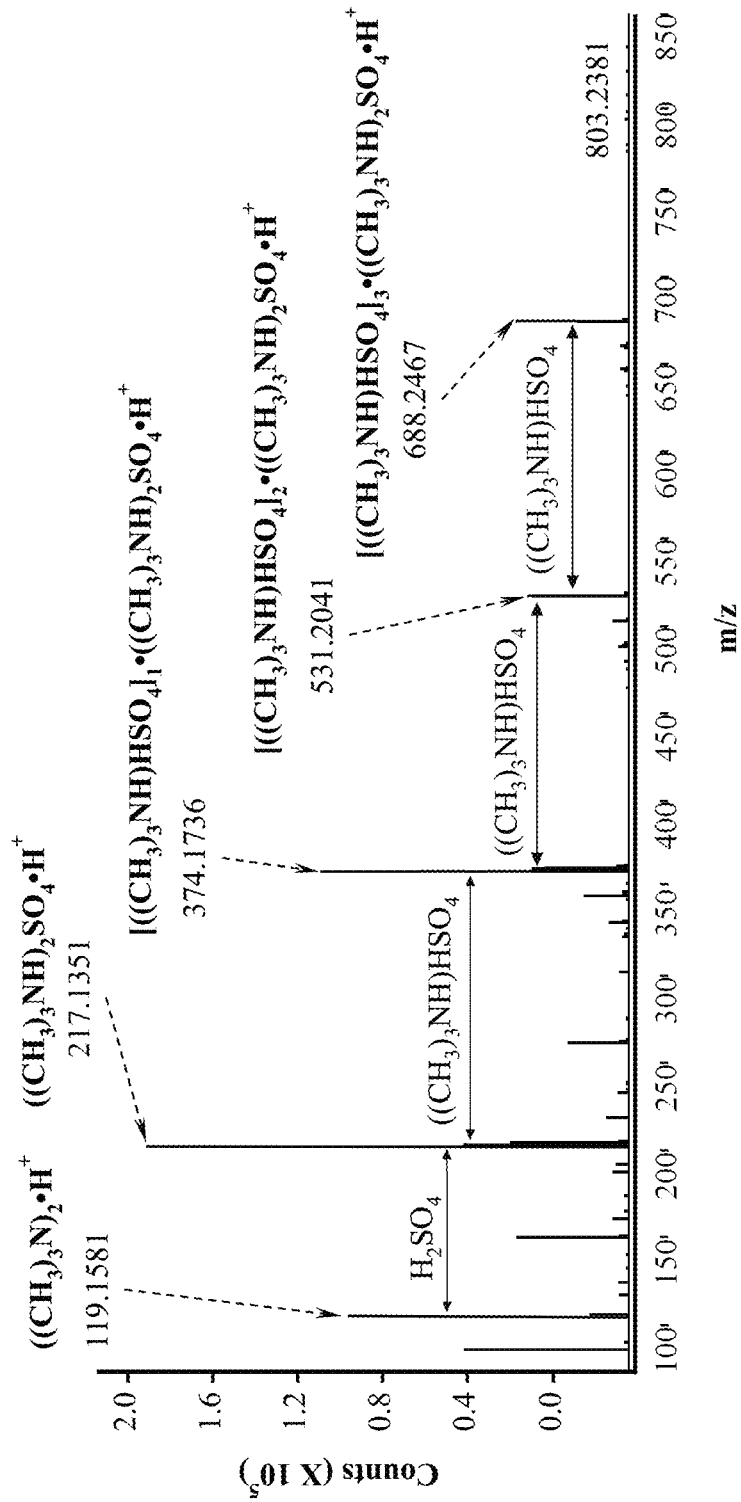
FIG. 9 is an ESI-MS spectrum of one example of a cluster compound as described herein, $R=CH_3$, a=3, b=0.

FIG. 9 is an ESI-MS spectrum of the trimethyl amine intermediate aqueous product. The spectrum includes major peaks at about m/z=217, 374, 531 and 688. The peak at about m/z=217 is consistent with protonated trimethyl amine sulfate, $((CH_3)_3NH)_2SO_4H^+$. The separation between adjacent major peaks is equal to the mass of trimethyl amine bisulfate, $(CH_3)_3NHHSO_4$. Thus, the spectrum is consistent with an intermediate aqueous product including cluster compounds having the formula $((CH_3)_3NH)_2SO_4\cdot(((CH_3)_3NH)HSO_4)_n$, where n=0 to 3. The spectrum also indicated a fragment with a m/z=119.1581, which is consistent with $((CH_3)_3N)_2\cdot H^+$. This type of fragment was not observed with the monomethyl or dimethyl amine analogs.

Figure 10:
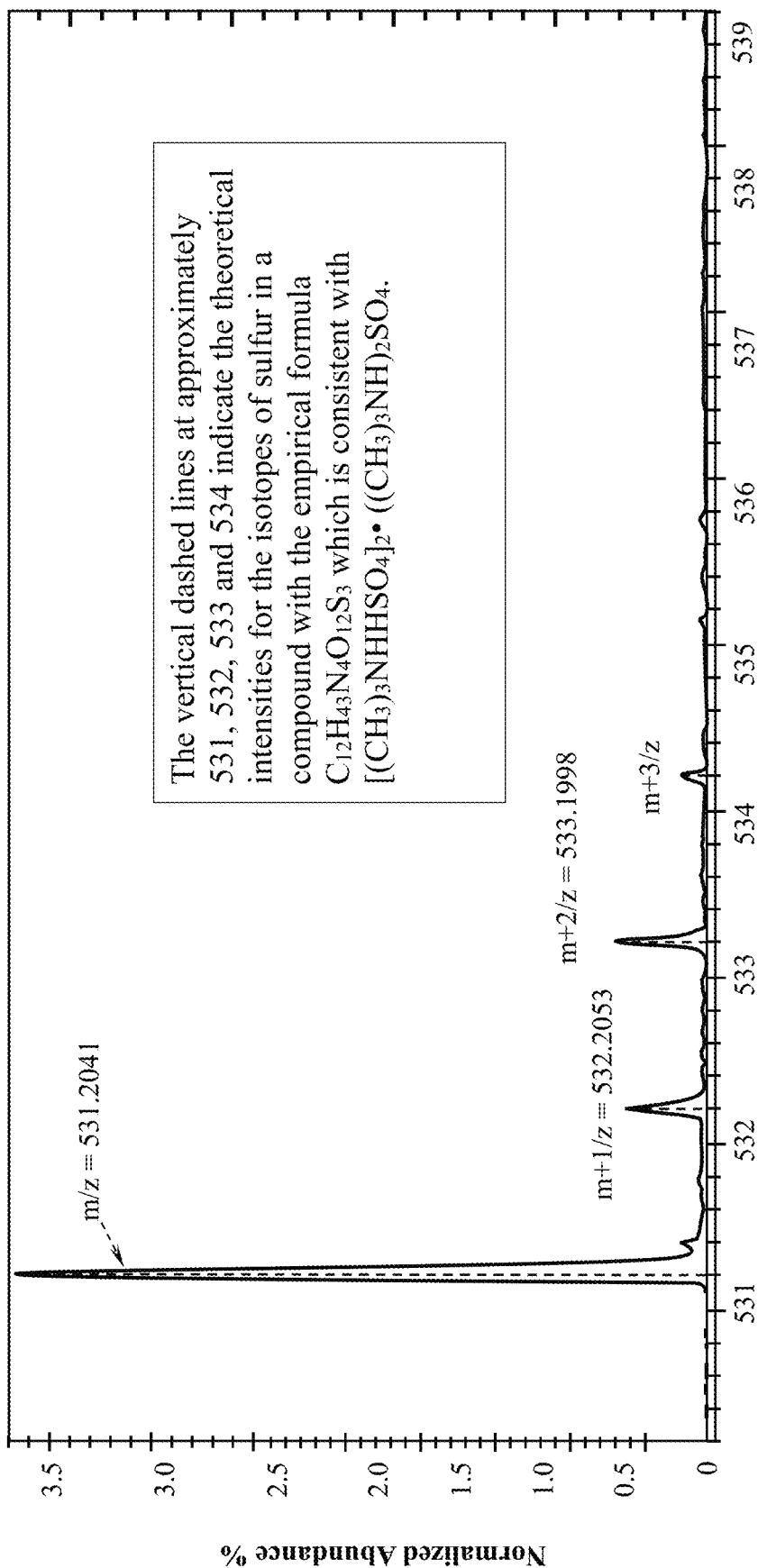
FIG. 10 is an expanded view of the High Resolution Mass spectrum shown in FIG. 9 from about m/z=530 to about m/z=539, showing the Isotopes of Sulfur, $R=CH_3$, a=3, b=0.

FIG. 10 is an expanded portion of the ESI-MS spectrum shown in FIG. 9 from about m/z=530 to about m/z=539. FIG. 10 indicates three sulfur atoms in the compound that is represented by the molecular ion peak, M (m/z=531.2041), and the isotope peaks M+1 (m/z=532.2053), M+2 (m/z=533.1998), and M+3 (m/z=534.2). The vertical lines inside the spectrum peaks indicate the theoretical intensities for the isotopes of sulfur ($^{33}S$ and $^{34}S$) in a compound with the molecular formula $(((CH_3)_3NH)HSO_4)_2\cdot((CH_3)_3NH)_2SO_4$, which is consistent with the empirical formula $C_{12}H_{43}N_4O_{12}S_3$. The measured intensities are consistent with the theoretical intensities, so the spectrum is consistent with the empirical formula, indicating a compound with three sulfur atoms.

Figure 11:
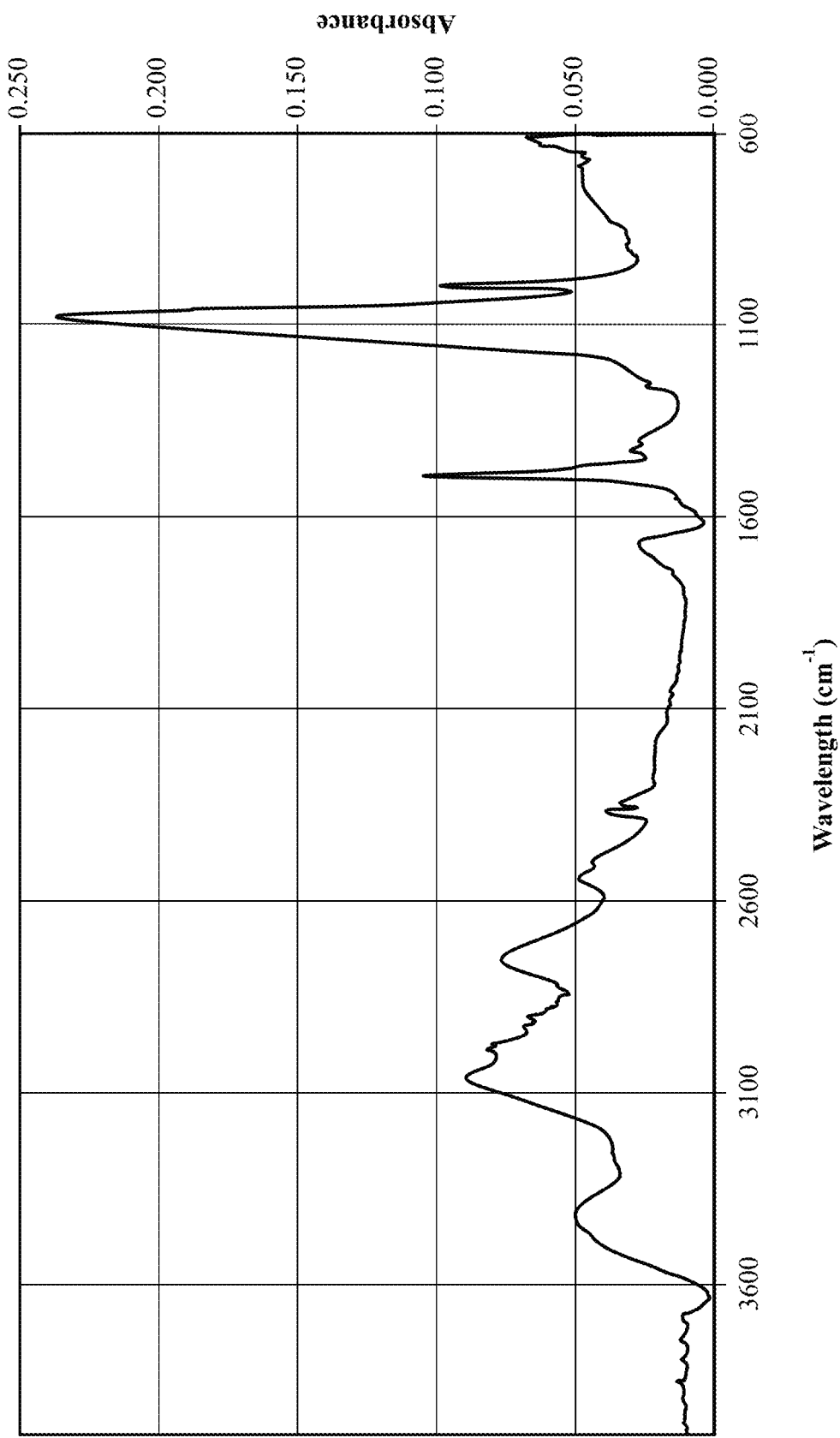
FIG. 11 is an IR spectrum of one example of a cluster compound as described herein after first acid addition, $R=CH_3$, a=3, b=0.

FIG. 11 is an IR spectrum of the trimethyl amine intermediate aqueous product. In FIG. 10, the peaks at 3400 and 1483 $cm^{-1}$ are consistent with N—H stretching and the peak at 1091 $cm^{-1}$ is consistent with a sulfate S=O stretching.

The ESI-MS and IR analyses of the trimethyl amine intermediate aqueous product confirm the presence of molecular cluster compounds having the formula $((CH_3)_3NH)_2SO_4\cdot(((CH_3)_3NH)HSO_4)_n$, where n=0 to 3.

As in Example 1, the remainder of the trimethyl amine intermediate aqueous product was treated with a second portion of sulfuric acid. As in Example 1, the molar ratio of the second portion of sulfuric acid to amine was 2.3:1.

The density of the final aqueous product was 1.295 g/ml. The observed sulfate concentration of the final aqueous product was 542,500 mg/L and the theoretical sulfate concentration was 567,439 mg/L. The final aqueous product was diluted 50 to 1, and the pH of the diluted final aqueous product was measured to be 1.23.

All patents, publications, and abstracts cited above are incorporated herein by reference in their entireties. Various embodiments of the invention have been described in fulfillment of the various objectives of the invention. It should be recognized that these embodiments are merely illustrative of the principles of the present invention. Numerous modifications and adaptions thereof will be readily apparent to those skilled in the art without departing from the spirit and scope of the present invention as defined in the following claims.

What is claimed is:

1. A solution comprising a plurality of cluster compounds, each cluster compound comprising a cluster of molecules comprising at least one substituted amine sulfate molecule of formula $(R_aNH_{4-a})_2SO_4$ and at least one substituted amine bisulfate molecule of formula $R_aNH_{4-a}HSO_4$, wherein in each amine sulfate and amine bisulfate molecule each R independently is either an alkyl substituent consisting of 1 to 6 carbon atoms or an aryl substituent and a is 1, 2, or 3, wherein the solution further comprises water, and wherein the cluster compounds are present in a concentration from about 5% to about 50% by weight.

2. The solution of claim 1, wherein the substituted amine sulfate molecule and the substituted amine bisulfate molecule each comprise at least one R that is an alkyl substituent consisting of 1 to 6 carbon atoms.

3. The solution of claim 2, wherein the at least one alkyl substituent is a methyl, ethyl, propyl, butyl, or pentyl group.

4. The solution of claim 1, wherein the substituted amine sulfate molecule and the substituted amine bisulfate molecule each comprise at least two R's that are alkyl substituents consisting of 1 to 6 carbon atoms.

5. The solution of claim 4, wherein the at least two R's are the same.

6. The solution of claim 4, wherein the at least two R's are different.

7. The solution of claim 1, wherein the substituted amine sulfate molecule and the substituted amine bisulfate molecule each comprise at least one R that is an aryl substituent.

8. The solution of claim 7, wherein the aryl substituent comprises 4 to 20 carbon atoms.

9. The solution of claim 1, wherein in each of the substituted amine sulfate molecule and the substituted amine bisulfate molecule a is 2 or 3.

10. The solution of claim 1, wherein the cluster of molecules further comprises at least one sulfuric acid molecule.

11. The solution of claim 1, wherein the cluster of molecules further comprises at least one water molecule.

12. The solution of claim 1, wherein a is 1.

13. The solution of claim 1, wherein a is 2.

14. The solution of claim 1, wherein a is 3.

15. The solution of claim 1, wherein the substituted amine sulfate molecule and the substituted amine bisulfate molecule each comprise at least one R that is a methyl group, wherein the cluster of molecules comprises a ratio of the substituted amine sulfate molecules to the substituted amine bisulfate molecules of from 1:1 to 1:10, and wherein the substituted amine sulfate molecules have formula $(((CH_3)_c R_b NH_{(4-(c+b))})_2 SO_4)$ and the substituted amine bisulfate molecules have formula $((CH_3)_c R_b NH_{(4-(c+b))} HSO_4)_n$, wherein each R independently is either an alkyl substituent consisting of 1 to 6 carbon atoms or an aryl substituent; c is 1, 2, or 3; and b is 0, 1, or 2, provided c+b is 1, 2, or 3.

16. The solution of claim 15, wherein b is 0.

17. The solution of claim 15, wherein b is 1.

18. The solution of claim 15, wherein b is 2.

19. The solution of claim 16, wherein c is 1.

20. The solution of claim 16, wherein c is 2.

21. The solution of claim 16, wherein c is 3.

22. The solution of claim 1, wherein the cluster of molecules has formula $$((R_a NH_{4-a})_2 SO_4)_x \cdot (H_2 SO_4)_y \cdot (H_2 O)_z \cdot ((R_a NH_{4-a}) HSO_4)_n,$$

wherein each R independently is either an alkyl substituent consisting of 1 to 6 carbon atoms or an aryl substituent; a is 1, 2, or 3; x is at least 1; y is at least 1; z is from 0 to 5; and n is at least one.

23. The solution of claim 22, wherein x is from 1 to 5, y is from 1 to 5, and n is from 1 to 20.

24. The solution of claim 22, wherein at least one R is an alkyl substituent.

25. The solution of claim 24, wherein the at least one alkyl substituent is a methyl, ethyl, propyl, butyl, or pentyl group.

26. The solution of claim 25, wherein the at least one alkyl substituent is a methyl group.

27. The solution of claim 22, wherein each R is a methyl group.

28. The solution of claim 22, wherein at least one R is an aryl substituent.

29. The solution of claim 28, wherein the at least one aryl substituent comprises from 4 to 20 carbon atoms.

30. The solution of claim 1, wherein the solution has a pH below about 2.

31. The solution of claim 30, wherein the solution has a concentration from about 10% to about 50% by weight.

32. A method of forming the solution of claim 1, the method comprising
combining an amine of formula $R_a NH_{3-a}$ and sulfuric acid to form a reaction mixture, wherein the amine and sulfuric acid are combined in water; and
cooling the reaction mixture to form the solution comprising the plurality of cluster compounds.

33. The method of claim 32, wherein combining the amine and the sulfuric acid is carried out without temperature control.

34. The method of claim 32, wherein combining the amine and the sulfuric acid comprises adding an aqueous solution of the amine to water containing the sulfuric acid.

35. The method of claim 32, wherein the molar ratio of amine to sulfuric acid in the reaction mixture is about 2:1.

36. The method of claim 32, wherein the amine comprises at least one R that is an alkyl substituent consisting of 1 to 6 carbon atoms.

37. The method of claim 32, wherein the amine comprises monomethyl amine, dimethyl amine, or trimethyl amine.

38. The method of claim 32, wherein the amine comprises at least one R that is an aryl substituent.

39. The method of claim 38, wherein the at least one aryl substituent comprises from 4 to 20 carbon atoms.

40. The method of claim 39, wherein the at least one aryl substituent further comprises one or more heteroatoms.

41. The method of claim 40, wherein the one or more heteroatoms are selected from the group consisting of sulfur, nitrogen, and oxygen.

42. The method of claim 32, wherein the cluster compound comprises a ratio of the amine sulfate molecules to the amine bisulfate molecules of from 1:1 to 1:10, and wherein the amine sulfate molecules have a formula of $((R_a NH_{4-a})_2 SO_4)$ and the amine bisulfate molecules have a formula of $(R_a NH_{4-a} HSO_4)_n$, wherein each R independently is either an alkyl substituent consisting of 1 to 6 carbon atoms or an aryl substituent; and a is 1, 2, or 3.

43. The method of claim 32, further comprising,
adding additional sulfuric acid to the solution comprising the plurality of cluster compounds to form a second reaction mixture; and
cooling the second reaction mixture to form a product mixture.

44. The method of claim 43, wherein adding the additional sulfuric acid is carried out without temperature control.

45. The method of claim 44, wherein the second reaction mixture comprises a cluster compound of formula $$((R_a NH_{4-a})_2 SO_4)_x \cdot (H_2 SO_4)_y \cdot (H_2 O)_z \cdot ((R_a NH_{4-a}) HSO_4)_n,$$

wherein each R independently is either an alkyl substituent consisting of 1 to 6 carbon atoms or an aryl substituent; a is 1, 2, or 3; x is at least 1; y is at least 1; z is from 0 to 5; and n is at least one.

* * * * *